United States Patent [19]

Singer et al.

[11] Patent Number: 4,477,618
[45] Date of Patent: Oct. 16, 1984

[54] AMINOPLAST CURABLE COATING COMPOSITIONS CONTAINING SULFONIC ACID ESTERS AS LATENT ACID CATALYSTS

[75] Inventors: Debra L. Singer, Pittsburgh; Gregory J. McCollum, Glenshaw; Rostyslaw Dowbenko, Gibsonia; Roger M. Christenson, Gibsonia; Michael M. Chau, Gibsonia; Wen-Hsuan Chang, Gibsonia, all of Pa.

[73] Assignee: PPG Industries, Inc., Pittsburgh, Pa.

[21] Appl. No.: 427,402

[22] Filed: Sep. 29, 1982

[51] Int. Cl.$^3$ .............................................. C08F 8/36
[52] U.S. Cl. .................................. 524/157; 524/158; 525/351; 525/353
[58] Field of Search ............... 524/157, 158, 159, 160; 525/351, 353

[56] References Cited

U.S. PATENT DOCUMENTS

| | | | |
|---|---|---|---|
| 2,141,893 | 12/1938 | Zitscher et al. | 260/505 |
| 2,227,708 | 1/1941 | Cordier | 260/71 |
| 2,961,424 | 11/1960 | Mueller et al. | 260/45.2 |
| 3,293,324 | 12/1966 | Tropp et al. | 260/850 |
| 3,384,606 | 5/1968 | Dieterich et al. | 260/29.4 |
| 3,474,054 | 10/1969 | White | 260/15 |
| 3,732,273 | 5/1973 | Heine et al. | 260/456 R |
| 3,798,262 | 3/1974 | Ziegler et al. | 260/505 R |
| 3,840,591 | 10/1974 | Lee et al. | 260/505 R |
| 3,842,021 | 10/1974 | Grant et al. | 260/15 |
| 3,907,706 | 9/1975 | Robins | 252/431 |
| 3,979,478 | 9/1976 | Gallacher | 260/850 |
| 4,192,826 | 3/1980 | Beresniewicz et al. | 525/425 |
| 4,200,729 | 4/1980 | Calbo | 525/398 |
| 4,247,461 | 1/1981 | Lin et al. | 260/239.1 |
| 4,281,075 | 7/1981 | Chattha | 525/110 |
| 4,350,790 | 9/1982 | Chattha | 525/110 |

FOREIGN PATENT DOCUMENTS

| | | |
|---|---|---|
| 0033038 | 12/1980 | European Pat. Off. |
| 2229364 | 1/1974 | Fed. Rep. of Germany |
| 57-63357 | 4/1982 | Japan |
| 57-63358 | 4/1982 | Japan |
| 1361929 | 7/1974 | United Kingdom |
| 1413054 | 11/1975 | United Kingdom |
| 1560821 | 2/1980 | United Kingdom |

OTHER PUBLICATIONS

Matar and Mekkawy, "The Effect of Ring Size and 2-Methyl Substituents on the Rate of Elimination of Cycloalkyl Tosylates in Dimethyl Sulphoxide", Indian J. Chem., vol. 13, May 1975, pp. 530-531.
Kotani, "Pyrolysis and Acetolysis of Some Sulfonic Esters, Bulletin of the Chemical Society of Japan, vol. 39, Aug. 1966, pp. 1767-1773.
Matar and Mekkawy, "Effect of Ring Size and 2-Methyl Substituents on the Rate of Elimination of Cycloalkyl Tosylates in Dimethyl Sulfoxide", J. Indian Chem. Soc., vol. LI, Sep. 1974, pp. 839-840.

Primary Examiner—Paul R. Michl
Attorney, Agent, or Firm—Linda Pingitore

[57] ABSTRACT

A high solids, organic solvent based, sprayable coating composition which is capable of acid catalyzed crosslinking is composed of an active hydrogen-containing resin, a curing agent present externally and/or internally as a part of the active hydrogen-containing resin, and a catalytic amount of a non-ionic ester of a sulfonic acid. The sulfonic acid ester is represented by the following structural formula:

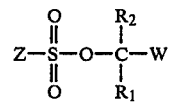

wherein:

Z is a radical selected from the group consisting of amino and an organic radical, said organic radical being connected to the sulfur atom by a carbon atom;

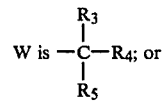

$C_3$–$C_{20}$ cycloalkyl; and $R_1$, $R_2$, $R_3$, $R_4$, $R_5$ are independently hydrogen or an organic radical. These groups can be particularly described as follows:

$R_1$ is hydrogen, carboalkoxy, $C_3$–$C_{20}$ alkyl, $C_6$–$C_{18}$ aryl, or $C_3$–$C_{20}$ cycloalkyl;

$R_2$ is hydrogen, carboalkoxy, $C_3$–$C_{20}$ alkyl, $C_6$–$C_{18}$ aryl, or $C_3$–$C_{20}$ cycloalkyl;

$R_3$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl;

$R_4$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl, and $R_5$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl.

20 Claims, No Drawings

AMINOPLAST CURABLE COATING COMPOSITIONS CONTAINING SULFONIC ACID ESTERS AS LATENT ACID CATALYSTS

BACKGROUND OF THE INVENTION

Coating compositions which are capable of acid catalyzed crosslinking generally contain a catalytic amount of an acid catalyst. The acid catalyst is added in order to accelerate crosslinking and thereby reduce the overall time required for cure. When an acid catalyst is utilized, it is advantageous to have the catalyst present as the free acid since in this manner a rapid cure can be efficiently achieved. However, the presence of the free acid may also cause problems in storage stability; that is, the coating composition will exhibit a tendency to gel and harden during the storage term, thus becoming unfit for use.

As a means of circumventing these difficulties, latent or blocked acid catalysts are often utilized to delay the action of crosslinking agents and otherwise postpone the curing mechanism.

Latent acid catalysts are formed by preparing a derivative of an acid catalyst such as para-toluenesulfonic acid (pTSA) or other sulfonic acids. For example, a well-known group of blocked acid catalysts are amine salts of aromatic sulfonic acids, such as pyridinium para-toluenesulfonate. Such sulfonate salts are less active than the free acid in promoting crosslinking. During cure, the catalysts are activated by heating which results in liberation of the free sulfonic acid catalyst.

The compositions of U.S. Pat. No. 4,192,826 and U.S. Pat. No. 4,281,075 are exemplary of coating compositions which utilize a latent acid catalyst to delay the action of the crosslinking agent until cure. U.S. Pat. No. 4,192,826 is directed to thermosetting liquid coating compositions based on polymer capable of being crosslinked with nitrogen resin crosslinkers, and blocked acid catalyst prepared from materials containing at least one oxirane functionality and a sulfonic acid. The blocked acid catalyst resulting from these reactants is a beta-hydroxy sulfonic acid ester. U.S. Pat. No. 4,281,075 is directed to thermosetting compositions based on a film-forming component bearing or capable of generating hydroxyl functionality, amine-aldehyde crosslinking agent, and a latent acid catalyst having the formula:

$$R-(SO_2)-O-X$$

wherein R is selected from alkyl or aryl groups and X is selected from 2-hydroxycycloalkyl and aryl substituted 2-hydroxycycloalkyl groups. The latent acid catalysts depicted by this formula are also beta-hydroxy sulfonic acid esters.

Also exemplary of coating compositions utilizing latent acid catalysts are GB Pat. No. 1,361,929 and GB Pat. No. 1,413,054.

SUMMARY OF THE INVENTION

In accordance with the present invention a class of non-ionic sulfonic acid esters is disclosed which are effective as latent acid catalysts in high solids, organic solvent based coating compositions. The claimed coating compositions have a total solids content of at least 50 percent and are sprayable. The aforesaid sulfonic acid esters are represented by the following structural formula

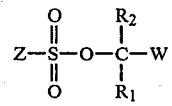

wherein Z is a radical selected from the group consisting of amino and an organic radical, said organic radical being connected to the sulfur atom by a carbon atom.

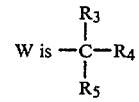

or $C_3$–$C_{20}$ cycloalkyl. $R_1$, $R_2$, $R_3$, $R_4$ and $R_5$ are independently hydrogen or an organic radical. These groups can be particularly described in the following manner:

- $R_1$ is hydrogen, carboalkoxy, $C_3$–$C_{20}$ alkyl, $C_6$–$C_{18}$ aryl, or $C_3$–$C_{20}$ cycloalkyl;
- $R_2$ is hydrogen, carboalkoxy, $C_3$–$C_{20}$ alkyl, $C_6$–$C_{18}$ aryl, or $C_3$–$C_{20}$ cycloalkyl;
- $R_3$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl;
- $R_4$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl, and
- $R_5$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl. The present invention also relates to a process of electrostatically spraying a substrate with a high solids, organic solvent based coating composition containing as an essential ingredient a latent acid catalyst of the claimed invention.

The sulfonic acid esters of the present invention have not heretofore been contemplated for use as latent acid catalysts in high solids, organic solvent based coating compositions. Moreover, the claimed sulfonic acid esters are readily distinguished from the aforedescribed art-recognized blocked acid catalysts prepared from a sulfonic acid and a material containing an oxirane functionality. Not only are the catalysts of the present invention beta-hydroxy free compounds and more stable relative to analogous beta-hydroxy esters, but they are also more versatile compounds. As a result of the vast range of materials which can be esterified with the sulfonic acid, catalysts can be prepared to suit particular needs. For example, by a studied choice of materials one can prepare a latent acid catalyst with increased stability at higher temperatures or a catalyst with increased catalytic activity. Moreover, the catalysts of the claimed invention result in coating compositions with improved storage stability, and can also impart such qualities as improved gloss as well as durability, flexibility and/or chemical resistance.

DETAILED DESCRIPTION OF THE INVENTION

The present invention is directed to organic solvent based, high solids, sprayable coating compositions containing as an essential ingredient a sulfonic acid catalyst of the following structural formula:

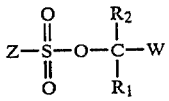

In the above formula Z is a radical selected from the group consisting of amino and an organic radical, said organic radical being connected to the sulfur atom by a carbon atom. The amino group represented by Z can also be substituted as follows:

wherein $R_6$ and $R_7$ are independently $C_1$–$C_{20}$ alkyl, $C_3$–$C_{20}$ cycloalkyl, and a heterocyclic moiety. When Z is an organic radical, it is exemplified by the following list: $C_1$–$C_{20}$ aliphatic, aromatic, and heterocyclic radicals. It should be understood that the aforementioned aliphatic, aromatic, and heterocyclic radicals can be substituted, said substituents including Cl, $NO_2$, $C_1$–$C_{20}$ alkyl, $OCH_3$, $CO_2X$ and $SO_3Y$, wherein X and Y are $C_1$–$C_{20}$ aliphatic, aromatic, and heterocyclic radicals and inorganic cations; X is also hydrogen.

In the above formula W can be

or $C_3$–$C_{20}$ cycloalkyl. It should be understood that the aforesaid cycloalkyl radical can be substituted with various substituents as long as they do not detract from the properties of the compound of Formula I. For example, W can be a methylcyclohexyl radical.

$R_1$, $R_2$, $R_3$, $R_4$ and $R_5$ are independently hydrogen or an organic radical. These groups can be more particularly described in the following manner:

$R_1$ is hydrogen, carboalkoxy, $C_1$–$C_{20}$ alkyl, $C_6$–$C_{18}$ aryl, or $C_3$–$C_{20}$ cycloalkyl;

$R_2$ is hydrogen, carboalkoxy, $C_1$–$C_{20}$ alkyl, $C_6$–$C_{18}$ aryl, or $C_3$–$C_{20}$ cycloalkyl;

$R_3$ is hydrogen, alkoxy, carboalkoxy, acyloxy, N-alkylcarbamyloxy, N-arylcarbamyloxy, $C_1$–$C_{20}$ alkyl, $C_6$–$C_{18}$ aryl, or $C_3$–$C_{20}$ cycloalkyl;

$R_4$ is hydrogen, alkoxy, carboalkoxy, acyloxy, N-alkylcarbamyloxy, N-arylcarbamyloxy, $C_1$–$C_{20}$ alkyl, $C_6$–$C_{18}$ aryl, or $C_3$–$C_{20}$ cycloalkyl; and $R_5$ is hydrogen, alkoxy, carboalkoxy, acyloxy, N-alkylcarbamyloxy, N-arylcarbamyloxy, $C_1$–$C_{20}$ alkyl, $C_6$–$C_{18}$ aryl, or $C_3$–$C_{20}$ cycloalkyl.

It should be understood that the aforesaid alkyl radicals may be substituted with various substituents which do not detract from the properties of the compound of formula (I). For example, $R_1$ can be a substituted alkyl having $Z$-$SO_3$ as the substituent, wherein Z is as defined above.

Substituents represented by Z include, for example, amino, cyclohexyl amino, methyl, ethyl, phenyl, p-tolyl, benzyl, o-carbomethoxyphenyl, naphthyl, and dinonylnaphthyl; preferably methyl, p-tolyl, phenyl, naphthyl, dinonylnaphthyl and o-carbomethoxyphenyl.

Substituents represented by $R_1$ and $R_2$ include, for example, hydrogen, methyl, ethyl, propyl, isopropyl, butyl, isobutyl, hexyl, 1-isobutyryloxy-2-methyl-2-propyl, 1,1-dimethyl-2-hydroxyethyl, carbomethoxy, carboethoxy, phenyl, and naphthyl.

Substituents represented by $R_3$, $R_4$ and $R_5$ include, for example, hydrogen, methyl, ethyl, propyl, isopropyl, butyl, isobutyl, hexyl, 2-ethylhexyl, 2-hydroxyethyl, isobutyryloxymethyl, methoxy, ethoxy, hexyloxy, 2-hexyloxyethoxy, carbomethoxy, carboethoxy, acetoxy, benzoxy, isobutyryloxy, N-phenylcarbamyloxy, N-butylcarbamyloxy, N-cyclohexylcarbamyloxy, methanesulfonyloxymethyl para-toluenesulfonyloxymethyl, o-carbomethoxybenzenesulfonyloxymethyl, and 2-hydroxyethylthio.

Preferred substituents for $R_1$ and $R_2$ include: hydrogen, methyl, ethyl, propyl, isopropyl, isobutyryloxymethyl and carboethoxy.

Preferred substituents for $R_3$, $R_4$ and $R_5$ include hydrogen, 2-hexyloxyethoxy, acetoxy, methanesulfonyloxymethyl and N-butylcarbamyloxy.

Exemplary of specific latent acid catalysts represented by the structural formula (I) include: 2,2,4-trimethyl-1,3-pentanediyl dimethanesulfonate, 1,2-butanediyl dimethanesulfonate, 1-carboethoxy ethyl methanesulfonate, 3-hydroxy-2,2,4-trimethylpentyl methanesulfonate, 2-ethyl-1,3-hexanediyl dimethanesulfonate, 2,2-dimethyl-1,3-pentanediyl bis-paratoluenesulfonate, 2,2,4-trimethyl-1,3-pentanediyl bis(orthocarbomethoxybenzenesulfonate), and 1-isobutyryloxy-2,2,4-trimethylpentane-3-yl paratoluenesulfonate.

Preferred compounds for use as catalysts in accordance with the claimed invention include: 2,2,4-trimethyl-1,3-pentanediyl dimethanesulfonate, 1-carboethoxy ethyl methanesulfonate, and 2,2,4-trimethyl-1,3-pentanediyl bis(ortho-carbomethoxybenzenesulfonate).

A significant aspect of the claimed invention is that the catalysts are beta-hydroxy free sulfonic acid esters; that is, sulfonic acid esters lacking a hydroxyl group on the carbon atom beta to the sulfonic acid ester linkage. It is theorized that because the catalysts lack such a hydroxyl group they are more stable compounds than the conventional latent acid catalysts containing a beta-hydroxyl group. Applicants' claimed catalysts are more stable relative to analogous beta-hydroxy esters since, for example, they exhibit resistance to etherification and to elimination to form an epoxide, both reactions being facilitated by the presence of a beta-hydroxyl group. As a result of this increased stability, not only do the catalysts of the subject invention facilitate single package coating compositions thus eliminating the difficulties associated with "on-the-job" mixing of catalyst with coating composition; but they also result in coating compositions which have extended shelf life.

The latent acid catalysts for use in the present invention can be produced from the reaction of an alcohol and a sulfonic acid chloride in the presence of an organic solvent and an acid acceptor. Examples of suitable alcohols employed in preparing the claimed latent acid catalysts include 2-butanol; 3-hydroxy-2,2,4-trimethylpentyl 2-methylpropionate; 2-propanol; 2-hexyloxyethanol; 2-ethyl-1,3-hexanediol; 2,2'-thiodiethanol; 2,2,4-trimethyl-1,3-pentanediol; ethyl L-lactate; 1,2-butanediol; and 2,2-dimethyl-1,3-pentanediol. Suitable solvents include methylene chloride, 1,1,1-trichloroethane, toluene, and xylene. Exemplary of suitable acid acceptors include pyridine, triethylamine, sodium hydroxide, potassium hydroxide, sodium methoxide, sodium hydride, sodiium metal, potassium hydride, and potassium t-butoxide.

The latent acid catalysts of the present invention can be used in organic solvent based, high solids coating compositions. Furthermore, the coating compositions are of the type which undergo acid catalyzed crosslinking and are cured at or above the temperature at which the sulfonate esters become catalytically active.

By high solids is meant that the coating composition has a total solids content of at least 50 percent. Moreover, the coating composition is sprayable at this level of solids. The sprayability is determined by spraying out the coating composition using a spray gun such as a suction spray gun operating at 60 psi with a No. 30 air cap and observing the mist produced. Above the maximum total solids content, the spray strings, forms chunk-like particles, and gives a web-like spray pattern.

It is essential that the coating composition be organic solvent based since the catalysts of the invention are unstable in aqueous media. Any organic solvent cnventionally utilized in the coatings art can be used herein. For example, suitable solvents include methyl ethyl ketone, methyl amyl ketone, methyl isobutyl ketone, methyl alcohol, ethyl alcohol, ethylene glycol monoethyl ether, ethylene glycol monoethyl ether acetate, and 2-ethylhexyl acetate.

The claimed compositions comprise an active hydrogen-containing resin, a curing agent present externally and/or internally as a part of the active hydrogen-containing resin, and a catalytic amount of a blocked acid catalyst of Formula I. The active hydrogen-containing resin is preferably a polymeric polyol having a hydroxyl functionality of at least two. Hydroxyl functionality is defined to be $$\frac{\text{number average molecular weight}}{\text{hydroxyl equivalent weight of polyol}}$$

Examples of useful polymeric polyols include hydrocarbon polyols, ester polyols, ether polyols, polyester polyols, polyether polyols, amide polyols, polyamide polyols, urethane polyols, polyurethane polyols, acrylic polyols, urea polyols, polyurea polyols, cyclic nitrogen-containing polyols and mixtures thereof; with the preferred polyols being the low molecular weight acrylic and polyester polyols and also polyurethane polyols. The aforesaid classes of polyols are described in detail in the following paragraphs.

Hydrocarbon polyols include trimethylolpropane; trimethylolethane; glycerol; 1,2,4-butane triol; 1,2,6-hexane triol; erythritol; sorbitol; mannitol; and diglycerol.

Ester polyols are obtained by reacting a polyol with one mole or less of a monocarboxylic acid. The polyols have a hydroxyl functionality of at least 3.0, examples of which are described immediately above. Suitable monocarboxylic acids include benzoic acid, hexanoic acid, octanoic acid, decanoic acid. Lauric acid, myristic acid, stearic acid, oleic acid, linoleic acid and linolenic acid can be used, but are less desirable.

Useful ether polyols are made by reacting a suitable polyol as described above with a monoepoxide, e.g., ethylene oxide, propylene oxide, butyl glycidyl ether, octyl glycidyl ether, allyl glycidyl ether, phenyl glycidyl ether, 1,2-butylene oxide, styrene oxide, glycidyl acrylate, and glycidyl methacrylate.

Polyester polyols are generally formed by the esterification of polyols with polycarboxylic acids or acid anhydrides. The polyols conventionally employed in making the polyester polyols include alkylene glycols, such as ethylene glycol, propylene glycol, butylene glycol and neopentyl glycol, and other glycols such as hydrogenated bisphenol A, cyclohexanedimethanol, caprolactone-diol reaction products, hydroxyalkylated bisphenols, polyether glycols, e.g., poly(oxytetramethylene) glycol, and similar type compounds. Other diols of various types and polyols of higher functionality can also be used. Such higher polyols include trimethylolpropane, trimethylolethane, pentaerythritol and higher molecular weight polyols, such as obtained by the reaction product of ethylene oxide and trimethylolpropane and various hydrolyzed epoxide resins.

Suitable carboxylic acids used in the reaction with the abovedescribed polyols include phthalic, isophthalic, terephthalic, tetrahydrophthalic, hexahydrophthalic, adipic, azelaic, sebacic, maleic, glutaric chlorendic, tetrachlorophthalic, fumaric, itaconic, malonic, suberic, 2-methylsuccinic, 3,3-diethylglutaric, 2,2-dimethylsuccinic acid and trimellitic acid. Anhydrides of these acids where they exist can also be employed and are encompassed by the term "carboxylic acid". Monocarboxylic acids such as benzoic acid and hexanoic acid can also be used, provided the average functionality of the polyol is above about 2.0. Saturated acids (including those aromatic acids where the only unsaturation is in the aromatic ring) are preferred.

It is also possible to produce polyester polyols containing one or two alkylene oxide groups per hydroxy group and preferably no more than three alkylene oxide groups per ester group. The alkylene oxide-derived polyester polyol can be produced by substituting an alkylene oxide-derived polyol for all or part of the polyol component used to produce the polyester polyol. Useful alkylene oxide-derived polyols include diethylene glycol, triethylene glycol, dipropylene glycol, tetraethylene glycol, 2,2-bis(hydroxyethoxyphenyl) propane and 2,2-bis(beta-hydroxypropoxyphenyl) propane. These polyester polyols can also be produced by oxalkylating any one of the above-described polyester polyols.

Polyester polyols can also be made from the reaction of a lactone with a polyol. The lactones, commercially available, are represented by the structure:

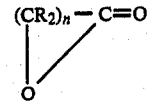

wherein n is from 2 to 9 and the R's are hydrogen, alkyl, cycloalkyl, alkoxy and single ring aromatic hydrocarbon radicals. Preferred lactones are the epsilon-caprolactones where n equals 5. Polyols, such as the above-described diols and triols are used in the reaction with the lactone.

Examples of polyether polyols are polyalkylene ether polyols which include those having the following structural formula:

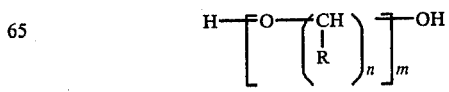

where the substituent R is hydrogen or lower alkyl containing from 1 to 5 carbon atoms including mixed substituents, n is from 2 to 6 and m is from 2 to 20. Included are poly(oxytetramethylene) glycols, poly(oxyethylene) glycols, poly(oxy-1,2-propylene) glycols and the reaction products of ethylene glycol with a mixture of 1,2-propylene oxide and ethylene oxide.

Also useful are polyether polyols formed from oxyalkylation of various polyols, for example, glycols such as ethylene glycol, 1,6-hexanediol, and bisphenol A, or other higher polyols, such as trimethylolpropane and pentaerythritol. Polyols of higher functionality which can be utilized as indicated can be made, for instance, by oxyalkylation of compounds such as sorbitol or sucrose. One commonly utilized oxyalkylation method is by reacting a polyol with an alkylene oxide, for example, ethylene or propylene oxide, in the presence of an acidic or basic catalyst.

Polyamide polyol resins useful in the instant invention are produced using conventional techniques. In general, the resins are produced from any of the above-described polyacids or lactones and diols, triols and higher alcohols and small amounts of diamines or amino alcohols. Suitable diamines and amino alcohols include hexamethylenediamine, ethylene-diamine, monoethanolamine, phenylenediamine, toluenediamine and diethanolamine. Amide polyols are also useful herein and are readily prepared by known methods.

Besides the above-mentioned polymeric polyols, polyurethane polyols can also be used. These polyols can be prepared by reacting any of the above-mentioned polyols with a minor amount of polyisocyanate (OH/NCO equivalent ratio greater than 1:1, preferably greater than about 2:1) so that free hydroxyl groups are present in the product. Mixtures of both high molecular weight and low molecular weight polyols may be used. Among the low molecular weight polyols are diols and triols such as aliphatic polyols including alkylene polyols containing from 2 to 18 carbon atoms. Examples include ethylene glycol, 1,4-butanediol, 1,6-hexanediol and cycloaliphatic polyols such as 1,2-hexanediol and cyclohexanedimethanol. Examples of triols include trimethylolpropane and trimethylolethane. Useful high molecular weight polyols are those described above. Also useful are polyols containing ether linkages such as diethylene glycol and triethylene glycol. Also, acid-containing polyols such as dimethylolpropionic acid and amino alkyl alcohols such as ethanol amine and diethanol amine can be used. In addition to the polyurethane polyols, urethane polyols can also be used and are readily prepared by known methods.

The organic isocyanate which is used to prepare the polyurethane polyols can be an aliphatic or an aromatic isocyanate or a mixture of the two. The aliphatic isocyanates are preferred when exterior durability is a requisite. Also, diisocyanates are preferred although higher polyisocyanates and monoisocyanates can be used in place of or in combination with diisocyanates. Examples of suitable higher polyisocyanates are 1,2,4-benzene triisocyanate and polymethylene polyphenyl isocyanate. Examples of suitable monoisocyanates are butyl isocyanate, cyclohexyl isocyanate, phenyl isocyanate and tolyl isocyanate. Examples of suitable aromatic diisocyanates are 4,4'-diphenylmethane diisocyanate, 1,3-phenylene diisocyanate, 1,4-phenylene diisocyanate and toluene diisocyanate. Examples of suitable aliphatic diisocyanates are straight chain aliphatic diisocyanates such as 1,4-tetramethylene diisocyanate and 1,6-hexamethylene diisocyanate. Also, cycloaliphatic diisocyanates can be employed. Examples include 1,4-cyclohexyl diisocyanate, isophorone diisocyanate, alpha,alpha'-xylylene diisocyanate and 4,4'-methylene-bis(cyclohexyl isocyanate).

The polyurea polyol resins are generally produced by reacting any of the above-described polyisocyanates with either an amino alcohol, such as monoethanol amine, or an amino alcohol and a diol. Urea polyols are also useful herein and are readily prepared by known methods.

Suitable cyclic nitrogen-containing polyols include such compounds as tris(hydroxyethyl) isocyanurate (THEIC), N,N'-bis(hydroxyethyl)-dimethyl hydantoin (BHDH), 1,4-bis[4,4-bis(hydroxymethyl)-1,3-oxazol-2-ene-2-yl]butane, hydroxyalkylated THEIC, hydroxyalkylated BHDH, bis(hydroxyethyl) ethylene urea, and 4,4-bis(hydroxymethyl)-1,3-oxazolidin-2-one.

Preferably, thermosetting acrylic polyols comprising the hydroxyalkyl esters of ethylenically-unsaturated carboxylic acids and at least one other ethylenically unsaturated monomer copolymerizable therewith, such as are described in U.S. Pat. Nos. 2,681,897 and 3,084,184 are used herein. Preferred interpolymers of the class described are those containing hydroxyalkyl esters in which the alkyl group has up to about 18 carbon atoms. Especially preferred esters are acrylic acid and methacrylic acid esters of ethylene glycol and 1,2-propylene glycol, i.e., hydroxyethyl acrylate and methacrylate, and hydroxypropyl acrylate and methacrylate. However, there may also be employed similar esters of other unsaturated acids, for example, ethacrylic acid, crotonic acid, and similar acids having up to about 6 carbon atoms, as well as esters containing other hydroxyalkyl radicals, such as hydroxybutyl esters and hydroxylauryl esters.

In addition to esters of unsaturated monocarboxylic acids, there may be employed the mono- or diesters of unsaturated dicarboxylic acids, such as maleic acid, fumaric acid and itaconic acid, in which at least one of the esterifying groups is hydroxyalkyl. Such esters include bis(hydroxyalkyl) esters, as well as various other alkylene glycol esters of such acids and mixed alkyl hydroxyalkyl esters, such as butyl hydroxyethyl maleate and benzyl hydroxypropyl maleate. The corresponding monoesters, such as the mono(hydroxyethyl), mono(hydroxypropyl), and similar alkylene glycol monoesters of maleic acid and similar acids, can also be used, and for some purposes are preferred.

The monomer or monomers with which the hydroxyalkyl ester is interpolymerized can be any ethylenic compound copolymerizable with the ester, the polymerization taking place through the ethylenically unsaturated linkages. These include monoolefinic and, in minor amounts, polyolefinic hydrocarbons, halogenated monoolefinic and diolefinic hydrocarbons, unsaturated esters of organic and inorganic acids, esters or amides of unsaturated acids, nitriles, unsaturated acids, and the like. Examples of such monomers include styrene; 1,3-butadiene; 2-chlorobutene; acrylonitrile; alpha-methylstyrene; alpha-chlorostyrene; 2-chlorobutadiene; 1,1-dichloroethylene; vinyl butyrate; vinyl acetate; vinyl chloride; allyl chloride; dimethyl maleate; divinyl benzene; diallyl itaconate; triallyl cyanurate; and the like. The preferred monomers are acrylates and methacrylates, such as ethyl acrylate, propyl acrylate, ethylhexyl acrylate, acrylamide, methyl methacrylate, butyl methacrylate, and the like, as well as methacrylic and acrylic acid.

Another important class of thermosetting acrylic resins that are used comprises the crosslinking carboxyl-containing polymers. The thermosetting carboxyl polymers that are used herein consist generally of acrylic resins or modified acrylic resins containing from about 3 to about 40 percent by weight of ethylenically unsaturated acid.

Acrylic materials which may be used include acrylates, such as ethyl acrylate, butyl acrylate, and hexyl acrylate; methacrylates, such as methyl methacrylate, isopropyl methacrylate, acrylonitrile, and hexyl methacrylate; maleate esters, such as dibutyl maleate; and fumarates, such as ethyl fumarate.

The ethylenically unsaturated acids which may be used are those such as acrylic acid, methacrylic acid, fumaric acid, maleic acid, and itaconic acid.

It should be understood that one may also employ as the active hydrogen-containing resin hydroxy functional vinyl resins or hydroxy functional alkyd resins which are well known to those skilled in the art. These resins can readily be prepared by art-recognized methods.

All of the above described curable polyols require a crosslinking agent to cure to a durable film. The crosslinking agent used with the above-described polyols is selected from the group consisting of aminoplast resins and phenoplast resins, with the aminoplast resins being preferred.

Aminoplast resins are based on the addition products of formaldehyde, with an amino- or amido-group carrying substance. Condensation products obtained from the reaction of alcohols and formaldehyde with melamine, urea or benzoguanamine are most common and preferred herein. However, condensation products of other amines and amides can also be employed, for example, aldehyde condensates of triazines, diazines, triazoles, guanadines, guanamines and alkyl- and aryl-substituted derivatives of such compounds, including alkyl- and aryl-substituted ureas and alkyl- and aryl-substituted melamines. Some examples of such compounds are N,N'-dimethyl urea, benzourea, dicyandimide, formaguanamine, acetoguanamine, glycoluril, ammeline, 2-chloro-4,6-diamino-1,3,5-triazine, 6-methyl-2,4-diamino-1,3,5-triazine, 3,5-diaminotriazole, triaminopyrimidine, 2-mercapto-4,6-diaminopyrimidine, 3,4,6-tris(ethylamino)-1,3,5-triazine, and the like.

While the aldehyde employed is most often formaldehyde, other similar condensation products can be made from other aldehydes, such as acetaldehyde, crotonaldehyde, acrolein, benzaldehyde, furfural, glyoxal and the like.

The aminoplast resins contain methylol or similar alkylol groups, and in most instances at least a portion of these alkylol groups are etherified by a reaction with an alcohol to provide organic solvent-soluble resins. Any monohydric alcohol can be employed for this purpose, including such alcohols as methanol, ethanol, propanol, butanol, pentanol, hexanol, heptanol and others, as well as benzyl alcohol and other aromatic alcohols, cyclic alcohol such as cyclohexanol, monoethers of glycols such as Cellosolves and Carbitols, and halogen-substituted or other substituted alcohols, such as 3-chloropropanol and butoxyethanol. The preferred aminoplast resins are substantially alkylated with methanol or butanol.

The phenolic resins which may be used as curing agents herein are formed by the condensation of an aldehyde and a phenol. The most used aldehyde is formaldehyde, although other aldehydes, such as acetaldehyde, can also be employed. Methylene-releasing and aldehyde-releasing agents such as paraformaldehyde and hexamethylene tetramine, can be utilized as the aldehyde agent if desired. Various phenols can be used; for instance, the phenol employed can be phenol per se, a cresol, or a substituted phenol in which a hydrocarbon radical having either a straight chain, a branched chain or a cyclic structure is substituted for a hydrogen in the aromatic ring. Mixtures of phenols are also often employed. Some specific examples of phenols utilized to produce these resins include p-phenylphenol, p-tert-butylphenol, p-tert-amylphenol, cyclopentylphenol and unsaturated hydrocarbon-substituted phenols, such as the monobutenyl phenols containing a butenyl group in ortho, meta or para position, and where the double bond occurs in various positions in the hydrocarbon chain. A common phenolic resin is phenol formaldehyde.

The ratio of the active hydrogen-containing resin to the crosslinking agent ranges from about 1:99 to about 99:1, preferably from about 1:9 to about 9:1.

In a preferred embodiment of the present invention a low molecular weight acrylic or polyester polyol is used as the active hydrogen-containing resin in conjunction with an at least partially methylated melamine-formaldehyde resin as aminoplast crosslinking agent.

In addition to the aforedescribed active hydrogen-containing resins which cure by means of external crosslinking agent, the active hydrogen-containing resin can also be a resin capable of curing by means of internal crosslinking without the use of an external crosslinking agent; for example, polyol-containing acrylic resins which are interpolymers of carboxylic acid amides. These acrylic resins comprise interpolymers of an unsaturated carboxylic acid amide with at least one other monomer having a $CH_2=C<$ group. Said interpolymers are characterized in that they have amido hydrogen atoms replaced by the structure—R-CHOR$_1$, wherein R is selected from the group consisting of hydrogen and saturated lower aliphatic hydrocarbon radicals and R$_1$ is a member of the class consisting of hydrogen and lower alkyl radicals with the proviso that the interpolymers have a hydroxyl number of at least 10. In general, these interpolymers can be produced in two ways. In the first method, the unsaturated carboxylic acid amide chosen is an N-alkoxymethyl acrylamide (i.e., a material having an —NHRCHOR$_1$ group in the molecule). This N-alkoxymethyl acrylamide is then polymerized with at least one other monomer having a $CH_2=C<$ group to produce a useful interpolymer. In the second method, an unsaturated carboxylic acid amide, e.g., acrylamide is polymerized with at least one other monomer having a $CH_2=C<$ group and is then reacted with an aldehyde to form a useful interpolymer.

Examples of useful interpolymers and their methods of manufacture are disclosed in U.S. Pat. Nos. 2,978,437; 3,037,963 and 3,079,434.

Among the monomers which may be polymerized with the unsaturated carboxylic acid amides are acrylates such as methyl acrylate, ethyl acrylate, isobutyl acrylate, and hexyl acrylate; styrene, vinyl toluene, maleate esters, such as dibutyl maleate; acidic materials such as acrylic acid, methacrylic acid, and maleic anhydride; vinyl ethers; vinyl ketones; vinyl pyridines; allyl acetoacetates; glycidyl acrylates; methacrylamide; dimethylbenzyl methacrylate; hydroxy-substituted acrylics, such as hydroxyethyl acrylate; and the adducts of epsilon-caprolactone and hydroxyalkyl acrylates. In general, a preferred group of monomers includes ethyl acrylate, butyl acrylate, methyl acrylate, styrene, vinyl toluene, acrylonitrile, acrylic acid, monomethyl styrene and hydroxyethyl acrylate.

It has been found that preferred unsaturated carboxylic acid amide interpolymers are obtained when at least two monomeric compounds are interpolymerized with the N-alkoxymethylacrylamide-containing or the amide-containing material. In this manner, it is possible to tailor the interpolymer to have any desired degree of hardness or flexibility. For example, one useful ternary interpolymer is prepared from the acrylamide, hydroxyethyl acrylate and methyl methacrylate, this interpolymer then being reacted with an aldehyde to produce a material useful in this invention.

It is known that small amounts of methyl methacrylate tend to improve the hardness of multi-component interpolymers where one of the monomers is of the type which forms soft homopolymers. It has also been found that a small quantity of an acid monomer, such as acrylic acid, methacrylic acid, crotonic acid, maleic acid or fumaric acid, is particularly useful as an internal catalyst in that it imparts to the coating composition desirable fast curing properties. In place of acrylamide, any other polymerizable amide, for example methacrylamide or itaconic diamide, may be utilized.

The N-alkoxymethyl acrylamides useful in this invention are known in the art, and include such materials as N-alkoxymethyl acrylamides, N-alkoxymethyl methacrylamides, N-methyl-N-alkoxymethylacrylamides, and the like. Specific examples include N-butoxymethylacrylamide, N-isobutoxymethylacrylamide, N-(methoxyethoxymethyl)acrylamide, and hydroxymethylacrylamide.

Although it is not required, if desired, external crosslinking agent can be added to the aforesaid interpolymers.

The coating compositions of the present invention can be cured thermally; whereupon heating, the liberation of the free sulfonic acid catalyst occurs. The temperature utilized for cure of the claimed coating compositions varies widely depending upon the structure of the particular sulfonate ester; although usually temperatures between about 100° C. and about 350° C. are utilized, preferably between about 100° C. and about 140° C. The length of time required for cure can also vary with the structure of the particular sulfonate ester; but from about 10 to about 60 minutes is typical. This broad variation in cure time and temperature as a function of the structure of the catalyst is significant evidence of the claimed catalysts' versatility. As a result of the broad range of available materials which can be esterified with a sulfonic acid catalyst, one can readily prepare a catalyst to suit many particular needs.

The amount of catalyst added to the coating compositions of the present invention is, generally, a catalytic amount, that is that amount required to accelerate the reaction to a commercially acceptable rate. Generally, 0.1 to 5 percent by weight on resin solids, preferably 0.5 to 2 percent, is added.

The coating compositions of the present invention can contain, in addition to an active hydrogen-containing resin, curing agent, and catalyst, other components to enhance various properties of the composition or the final coating. Examples of such components include pigments, pigment stabilizers, rheology control agents, dispersants, adhesion-promoting agents, colorants, and the like.

The coating compositions of this invention are useful for application on metallic substrates, such as steel or aluminum, and they can be applied with or without a primer. They can also be applied to other substrates such as plastics and wood. The compositions can be applied in any conventional manner, such as, spray-, dip-, roll-, or brush-coating. The claimed coating compositions are especially useful for electrostatic spray application. This is because the blocked acid catalysts of the present invention are non-ionic compounds; hence, they do not hamper the electrostatic spray characteristics of the coating composition. After the substrate is electrostatically sprayed it is typically baked at a temperature of from about 100° C. to about 350° C. to form a cured coating The claimed coating compositions not only facilitate "single-container" packaging, but they also provide improved storage stability. In addition they can also provide such qualities as improved gloss, good flexibility, durability and/or chemical resistance.

The following examples are submitted for the purpose of further illustrating the nature of the present invention and should not be construed as a limitation on the scope thereof. All parts and percentages in the Examples and throughout the specification are by weight unless otherwise indicated.

EXAMPLE I

Preparation of 2,2,4-trimethyl-1,3-pentanediyl dimethanesulfonate

A one liter, four-necked, round bottom flask, equipped with thermometer, addition funnels, condenser and stirrer was charged with 1400 parts of methylene chloride and 146 parts of 2,2,4-trimethyl-1-3-pentanediol (hereinafter referred to as TMPD) and these materials were thoroughly mixed. The flask was placed under a nitrogen atmosphere and cooled below 0° C. using a dry ice-acetone bath. Into an addition funnel was placed 228 parts of methanesulfonyl chloride and 50 parts of methylene chloride. A second addition funnel was charged with 202 parts of triethylamine and 50 parts of methylene chloride. The two addition funnels were simultaneously emptied, dropwise, into the cooled reaction flask containing TMPD and methylene chloride. After addition was complete, the reaction flask was held below 0° C. for two to three hours and subsequently placed in a cold room at about −5° C.

The reaction medium was brought to 0° C. and filtered through a sintered glass funnel using an aspirator. The solid filtercake containing triethylammonium salt was washed with small amounts of chilled methylene chloride and then discarded. The liquid methylene chloride containing filtrate was washed with an approximately equal volume of water to remove any water soluble impurities. An equal volume of water was then added. Concentrated sulfuric acid was added dropwise until an acid pH was achieved. The layers were then separated and the water layer was discarded. The methylene chloride layer was washed twice with dilute sodium bicarbonate, and then dried with sodium sulfate. It was then filtered and solvent removed in vacuo.

Identification of the TMPD dimethanesulfonate was performed by infrared spectroscopy. In order to crystallize TMPD-dimethanesulfonate, the liquid was chilled overnight at about 20° C. and then filtered to obtain a white solid. This solid was washed free of any solvents with small amounts of heptane and dried thoroughly by aspiration. Recrystallization to purify was done using a mixture of ethyl acetate and heptane. The melting point of TMPD-dimethanesulfonate prepared in this example was 84° C.

EXAMPLE II

A coating composition employing 2,2,4-trimethyl-1,3-pentanediyl dimethanesulfonate (prepared in Example I above) as latent acid catalyst was formulated in the following manner: Initially, the coating composition was made having the following formulation:

|  | Parts by Weight | Percent of Resin Solids |
|---|---|---|
| Film-forming resin (1) | 90 | 34 |
| TMPD - caprolactone (2) | 90 | 34 |
| Crosslinking agent (3) | 77 | 29 |
| Epoxy solution (4) | 8 | 3 |
| Titanium dioxide | 212 |  |

Subsequently, to 65 parts of this coating composition (56 percent resin solids and 74 percent total solids content) were added 4 parts of 2,2,4-trimethyl-1,3-pentanediyl dimethanesulfonate (15 percent resin solids) to make the final coating. The applied coating composition was cured by flashing for 10 minutes followed by baking for 10 minutes at 210° C. to yield a hard, glossy film.
(1) A polyester resin which is a copolymer of hexahydrophthalic anhydride/trimethylol propane diallyl ether/propylene oxide in a mole ratio of 1:1:2.6.
(2) 2,2,4-trimethyl-1,3-pentanediol caprolactone which is a copolymer of 44 percent of 2,2,4-trimethyl-1,3-pentanediol and 56 percent of caprolactone.
(3) An alkylated melamine-formaldehyde resin available as CYMEL 303 from American Cyanamid.
(4) A light stable epoxy available as DRH 151.1 from Shell Oil Corp.

EXAMPLE III

Preparation of 1,2-butanediyl dimethanesulfonate

Into a one liter, four-necked round bottom flask equipped with stirrer, condenser, thermometer, and addition funnel, 57.0 parts of methanesulfonyl chloride, 22.5 parts of 1,2-butanediol and 57.0 parts of methylene chloride were mixed under a nitrogen blanket and cooled to 0° C. using a dry ice-acetone bath. To this 50.5 parts of triethylamine was added over one hour. The reaction was stirred at 0° C. for an additional three hours and allowed to stand for 18 hours at 0° C. The mixture was vacuum filtered and then washed successively with chilled dilute sulfuric acid (twice with 200 part-portions), dilute sodium bicarbonate (three times with 200 part-portions), and water (twice with 200 part-portions), dried over sodium sulfate, filtered, and the solvent removed in vacuo at 35° C. to give the product as a pale yellow liquid.

EXAMPLE IV

Preparation of 1-carboethoxy ethyl methanesulfonate

Into a one liter, four-necked round bottom flask equipped with stirrer, condenser, thermometer, and addition funnel, 57.0 parts of methanesulfonyl chloride, 59.0 parts of ethyl L-lactate and 300.0 parts of methylene chloride were mixed under a nitrogen blanket and cooled to 0° C. using dry ice-acetone bath. To this, 50.5 parts of triethylamine was added over one hour. The reaction was stirred at 0° C. for an additional three hours and allowed to stand at 0° C. for 18 hours. The mixture was vacuum filtered and then washed successively with chilled dilute sulfuric acid (twice with 200 part-portions), dilute sodium bicarbonate (three times with 200 part-portions), and water (twice with 200 part-portions), dried over sodium sulfate, filtered, and the solvent removed in vacuo at 35° C. to give the product as a pale yellow liquid.

EXAMPLE V

Preparation of 2,2,4-trimethyl-1,3-pentanediyl bis(ortho-carbomethoxybenzenesulfonate)

Into a one-liter, four-necked, round bottom flask equipped with stirrer, condenser, thermometer and addition funnel, 36.5 parts of 2,2,4-trimethyl-1,3-pentanediol and 632.0 parts of pyridine were mixed under a nitrogen blanket and cooled to 0° C. using an ice water bath. Subsequently, 117.3 parts of o-carbomethoxybenzenesulfonyl chloride were added in small portions over a two hour period while maintaining the temperature below 10° C. The aforesaid mixture was maintained at a temperature between 0° C. and 10° C. for a two hour period and then refrigerated at 15° C. for at least twenty-four hours prior to work-up. For work-up the reaction mixture was poured into 1000 parts of ice water and subsequently extracted with 500 parts of methylene chloride. The organic layer was washed successively with cold, dilute 6N sulfuric acid (twice with 500 part-portions), cold, dilute sodium bicarbonate (once with 500 parts), and water (until the water layer was neutral to pH paper). It was then dried over sodium sulfate, filtered, and the solvent removed in vacuo to yield the 2,2,4-trimethyl-1,3-pentanediyl bis-(ortho-carbomethoxybenzenesulfonate).

EXAMPLE VI

Preparation of 1-isobutyryloxy-2,2,4-trimethylpentane-3-yl para-toluenesulfonate Into a one-liter, four-necked, round bottom flask equipped with stirrer, condenser, and thermometer, 200.0 parts of pyridine and 54.0 parts of 3-hydroxy-2,2,4-trimethylpentyl 2-methylpropionate were mixed under a nitrogen blanket and cooled to 0° C. using an ice water bath. To this, 57.0 parts of para-toluenesulfonyl chloride were added in portions over a thirty minute period. The solution was stirred for one hour at 0° C. and then allowed to stand for twenty-four hours at 15° C. The mixture was subsequently poured into one liter of ice water, which was then extracted with 700 parts of methylene chloride. The organic layer was washed successively with cold 6N sulfuric acid (until the water layer was acidic to pH paper); dilute sodium bicarbonate (three times with 500 part-portions); and water (twice with 500 part-portions). It was then dried over sodium sulfate, filtered, and the solvent removed in vacuo to yield the 1-isobutyryloxy-2,2,4-trimethylpentane-3-yl para-toluenesulfonate.

EXAMPLE VII

This example illustrates some physical properties of cured films of coating compositions incorporating the catalysts of the claimed invention. The base coating composition employed had a total solids content of 90 percent and was prepared in the following manner.

|  | Parts by Weight | Percent of Resin Solids |
|---|---|---|
| Pigment Paste (1) | 563 | 37 |
| Acrylic Resin (2) | 160 | 37 |
| Crosslinking Agent (3) | 86 | 26 |
| Silicone Surfactant (4) | 13 |  |
| Methyl Amyl Ketone | 55 |  |
| Cellosolve Acetate (5) | 10 |  |

(1) This pigment paste having a 22 percent resin solids content and a 92 percent total solids content was formulated by combining together: 500 parts of titanium dioxide pigment; 282 parts of acrylic resin (78 percent resin solids content in methyl amyl ketone and has a hydroxyl number of 67. It is commercially available from Rohm and Haas as ACRYLOID AT-400); 145 parts of butanol; and 73 parts of methyl amyl ketone.
(2) This thermosetting acrylic resin has a 78 percent resin solids content in methyl amyl ketone and has a hydroxyl number of 67. It is commercially available from Rohm Haas as ACRYLOID AT-400.
(3) Melamine-formaldehyde resin is commercially available as CYMEL-303 from American Cyanamid.
(4) Silicone surfactant (1% in toluene) is commercially available as S.F. 1023 from General Electric Corp.
(5) Commercially available from Union Carbide Corp.

The catalyst-containing composition was formulated by mixing together 292 parts of the aforedescribed base coating composition (38 percent resin solids and 90 percent total solids), 3 parts of cyclohexyl paratoluenesulfonate and 8 parts of methyl amyl ketone. The preparation of the catalysts utilized has been described in the preceding examples.

Each coating composition was applied with a 3 mil drawbar on a cold rolled steel panel treated with BONDERITE 1000. (Treated panels available from Hooker Chemical Co.)

Sward Hardness was calculated by averaging two separate readings. (The films designated as tacky were not tested for Sward Hardness).

The solvent resistance was evaluated after each panel underwent 20 double rubs with xylene. Ratings were as follows:
10—no effect
9-6—gloss marred
5—slight removal of film
4-1—increased film removal
0—complete film removal Gloss was measured with a gloss meter.

EXAMPLE VIII

This example illustrates hot room stabilities of selected latent acid catalysts of the claimed invention. Stability was based upon the length of time required for a sample of the coating composition described in Example V, above, containing catalyst to double in viscosity while in a hot room at 49° C. Each sample contained 1 percent catalyst by weight.

| Catalyst | Time to Double in Viscosity at 49° C. |
|---|---|
| None (control) | Greater than 4 weeks |
| Para-toluenesulfonic acid | Less than 1 day |
| ethyl propionate-2-yl methanesulfonate | 1 day |
| 1,2-butanediyl dimethanesulfonate | 2 days |
| 3-hydroxy-2,2,4-trimethylpentyl methanesulfonate | 4 days |
| 2,2,4-trimethyl-1,3-pentanediyl dimethanesulfonate | 2 days |
| 2,2,4-trimethyl-1,3-pentanediyl bis(ortho-carbomethoxybenzenesulfonate) | 6 days |

| | Cured at 120° C. | | | | | | Cured at 135° C. | | | | | |
|---|---|---|---|---|---|---|---|---|---|---|---|---|
| | 15 minutes | | | 30 minutes | | | 15 minutes | | | 30 minutes | | |
| Catalyst (1% active catalyst) by Weight | Sward Hardness | Xylene Resistance | Gloss | Sward Hardness | Xylene Resistance | Gloss | Sward Hardness | Xylene Resistance | Gloss | Sward Hardness | Xylene Resistance | Gloss |
| p-toluenesulfonic acid | 36 | 9 | 65 | 41 | 9 | 70 | 27 | 8 | 67 | 32 | 8 | 75 |
| 1,2 butandiyl dimethanesulfonate | tacky | 0 | 85 | | | | 4 | 0 | 78 | 4 | 0 | 80 |
| 1-carboethoxy ethyl methanesulfonate | 6 | 6 | 70 | 16 | 8 | 83 | 24 | 9 | 85 | 32 | 7 | 80 |
| 2,2,4-trimethyl-1,3-pentanediyl bis(ortho-carboxymethoxybenzenesulfonate) | 20 | 9 | 75 | 42 | 10 | 75 | 38 | 9 | 72 | 41 | 10 | 75 |
| 2,2,4-trimethyl-1,3-pentanediyl dimethanesulfonate | 43 | 9 | 78 | 47 | 9 | 80 | 40 | 10 | 84 | 45 | 10 | 78 |

| | | Cured at 150° C. | | | | |
|---|---|---|---|---|---|---|
| | | 15 minutes | | | 30 minutes | |
| | Catalyst (1% active catalyst) by Weight | Sward Hardness | Xylene Resistance | Gloss | Sward Hardness | Xylene Resistance | Gloss |
| | p-toluenesulfonic acid 1,2 butandiyl dimethanesulfonate 1-carboethoxy ethyl methanesulfonate 2,2,4-trimethyl-1,3-pentanediyl bis(ortho-carbomethoxybenzenesulfonate) 2,2,4-trimethyl-1,3-pentanediyl dimethanesulfonate | 8 | 4 | 79 | 10 | 6 | 78 |

What is claimed is:

1. An organic solvent based coating composition having a total solids content of at least 50 percent and which is sprayable, said coating composition being capable of acid catalyzed crosslinking, comprising an active hydrogen-containing resin, a curing agent present externally and/or internally as a part of the active hydrogen-containing resin, and a catalytic amount of a non-ionic ester of a sulfonic acid, represented by the following structural formula:

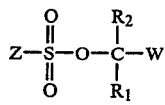

wherein:

Z is a radical selected from the group consisting of amino and an organic radical, said organic radical being connected to the sulfur atom by a carbon atom;

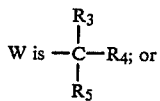

$C_3$–$C_{20}$ cycloalkyl; and $R_1$ is hydrogen, carboalkoxy, $C_3$–$C_{20}$ alkyl, $C_6$–$C_{18}$ aryl, or $C_3$–$C_{20}$ cycloalkyl;

$R_2$ is hydrogen, carboalkoxy, $C_3$–$C_{20}$ alkyl, $C_6$–$C_{18}$ aryl, or $C_3$–$C_{20}$ cycloalkyl;

$R_3$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl;

$R_4$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl, and $R_5$ is hydrogen, carboalkoxy, acyloxy, N-alkylcarbamyloxy, N-arylcarbamyloxy, $C_3$–$C_{20}$ alkyl, $C_6$–$C_{18}$ aryl, or $C_3$–$C_{20}$ cycloalkyl.

2. The composition of claim 1 wherein Z is a radical selected from the group consisting of $C_1$–$C_{20}$ aliphatic, aromatic, heterocyclic, amino and

wherein $R_6$ and $R_7$ are selected from the group consisting of $C_1$–$C_{20}$ alkyl, $C_3$–$C_{20}$ cycloalkyl, and a heterocyclic moiety.

3. The composition of claim 1 or 2 wherein W is

4. The composition of claim 1 wherein $R_1$, $R_2$, $R_3$, $R_4$, $R_5$ are independently sulfonate substituted alkyls.

5. The composition of claim 1 wherein the active hydrogen-containing resin is a polymeric polyol having a hydroxyl functionality of at least two.

6. The composition of claim 5 wherein the polymeric polyol is selected from the group consisting of hydrocarbon polyols, ester polyols, ether polyols, polyester polyols, polyether polyols, amide polyols, polyamide, polyols, acrylic polyols, urethane polyols, polyurethane polyols, cyclic nitrogen-containing polyols, urea polyols, polyurea polyols and mixtures thereof.

7. The composition of claim 1 wherein the curing agent is an aminoplast resin.

8. The composition of claim 7 wherein the aminoplast resin is a melamine-formaldehyde condensation product.

9. The composition of claim 8 wherein the aminoplast resin is an at least partially alkylated melamine-formaldehyde condensation product.

10. The composition of claim 9 wherein the aminoplast resin is at least partially methylated.

11. The composition of claim 9 wherein the polymeric polyol is a polyester polyol.

12. The composition of claim 9 wherein the polymeric polyol is an acrylic polyol.

13. The composition of claim 9 wherein the polymeric polyol is a polyurethane polyol.

14. The composition of claim 1 wherein the active hydrogen-containing resin is an interpolymer of a carboxylic acid amide with at least one other monomer having a $CH_2=C<$ group.

15. The composition of claim 1 wherein Z is selected from the group consisting of amino, cyclohexyl amino, methyl, ethyl, phenyl, p-tolyl, benzyl, o-carbomethyoxyphenyl, naphthyl, and dinonylnaphthyl.

16. The composition of claim 9 wherein:

$R_1$, $R_2$ are independently selected from the group consisting of hydrogen, propyl, isopropyl, 1-isobutyryloxy-2-methyl-2-propyl, and carboethoxy; and $R_3$, $R_4$, and $R_5$ are independently selected from the group consisting of hydrogen, methanesulfonyloxymethyl, N-butylcarbamyloxy, para-toluenesulfonyloxymethyl, isobutyrloxymethyl and ortho-carbomethoxybenzenesulfonyloxymethyl.

17. The composition of claim 4 wherein the sulfonic acid ester is 2,2,4-trimethyl-1,3-pentanediyl dimethanesulfonate.

18. The composition of claim 1 wherein the sulfonic acid ester is 1-carboethoxy ethyl methanesulfonate.

19. The composition of claim 1 wherein the sulfonic acid ester is 2,2,4-trimethyl-1,3-pentanediyl bis(ortho-carbomethoxybenzenesulfonate).

20. A process for coating a substrate with a high solids, organic solvent based, sprayable coating composition, comprising the steps of:

(a) electrostatically spraying a substrate with an organic solvent based, sprayable coating composition having a total solids content of at least 50 percent, comprising:
  (i) an active hydrogen-containing resin;
  (ii) a curing agent present either externally and/or internally as a part of the active hydrogen-containing resin; and
  (iii) a catalytic amount of a catalyst of the formula of claim 1;

(b) baking the coated substrate of step (a) at a temperature of about 100° C. to about 350° C. to form a cured coating.

* * * * *